United States Patent
Thomas (10) Patent No.: US 8,382,849 B2
(45) Date of Patent: Feb. 26, 2013

(54) POROUS TITANIUM TIBIAL SLEEVES AND THEIR USE IN REVISION KNEE SURGERY

(75) Inventor: Kyle Thomas, Fort Wayne, IN (US)

(73) Assignee: DePuy Synthes Products, LLC, Warsaw, IN (US)

( * ) Notice: Subject to any disclaimer, the term of this patent is extended or adjusted under 35 U.S.C. 154(b) by 123 days.

(21) Appl. No.: 12/476,431

(22) Filed: Jun. 2, 2009

(65) Prior Publication Data

US 2010/0057212 A1 Mar. 4, 2010

Related U.S. Application Data

(60) Provisional application No. 61/058,256, filed on Jun. 3, 2008.

(51) Int. Cl.
*A61F 2/38* (2006.01)
*A61F 2/28* (2006.01)

(52) U.S. Cl. ............... 623/20.34; 623/20.32; 623/16.11

(58) Field of Classification Search ............ 623/16.11, 623/20.32–20.34; *A61F 2/28, 2/38*
See application file for complete search history.

(56) References Cited

U.S. PATENT DOCUMENTS

| | | | |
|---|---|---|---|
| 2,947,308 A | 8/1960 | Gorman | |
| 4,136,405 A | 1/1979 | Pastrick et al. | |
| 4,523,587 A | 6/1985 | Frey | |
| 4,549,319 A | 10/1985 | Meyer | |
| 4,634,444 A | 1/1987 | Noiles | |
| 4,659,331 A | 4/1987 | Matthews et al. | |
| 4,711,639 A | 12/1987 | Grundei | |
| 4,790,852 A | 12/1988 | Noiles | |
| 4,822,366 A | 4/1989 | Bolesky | |
| 4,827,919 A | 5/1989 | Barbarito et al. | |
| 4,846,839 A | 7/1989 | Noiles | |
| 4,883,488 A | 11/1989 | Bloebaum et al. | |
| 4,888,021 A | 12/1989 | Forte et al. | |
| 4,944,757 A | 7/1990 | Martinez et al. | |
| 5,011,496 A | 4/1991 | Forte et al. | |
| 5,133,760 A | 7/1992 | Petersen et al. | |
| 5,152,796 A | 10/1992 | Slamin | |
| 5,197,488 A | 3/1993 | Kovacevic | |
| 5,211,664 A | 5/1993 | Tepic et al. | |
| 5,326,359 A | 7/1994 | Oudard | |
| 5,358,530 A | 10/1994 | Hodorek | |
| 5,387,241 A | 2/1995 | Hayes | |
| 5,405,395 A | 4/1995 | Coates | |
| 5,413,604 A | 5/1995 | Hodge | |

(Continued)

FOREIGN PATENT DOCUMENTS

| EP | 1004283 B1 | 5/2005 |
|---|---|---|
| EP | 1532945 A2 | 5/2005 |

(Continued)

OTHER PUBLICATIONS

European Search Report, European Patent Application No. 11178524.2-2310, Nov. 15, 2011, 5 pages.

(Continued)

*Primary Examiner* — Thomas J Sweet
*Assistant Examiner* — Jason-Dennis Stewart
(74) *Attorney, Agent, or Firm* — Barnes & Thornburg LLP (57) ABSTRACT

The invention concerns monolithic foam sleeves that comprises titanium or titanium alloy foam having a porosity of 50 to 85% and possesses a proximal surface, a distal end, an interior wall that defines an interior channel and extends from the proximal surface to the distal end; and a terraced outer surface that tapers such that said sleeve is widest at the proximal surface and most narrow at the distal end.

8 Claims, 4 Drawing Sheets

U.S. PATENT DOCUMENTS

| | | | |
|---|---|---|---|
| 5,462,550 | A | 10/1995 | Dietz et al. |
| 5,462,563 | A | 10/1995 | Shearer et al. |
| 5,480,445 | A | 1/1996 | Burkinshaw |
| 5,683,467 | A | 11/1997 | Pappas |
| 5,716,412 | A | 2/1998 | Decarlo et al. |
| 5,766,256 | A | 6/1998 | Oudard et al. |
| 5,782,921 | A | 7/1998 | Colleran et al. |
| 5,824,103 | A | 10/1998 | Williams |
| 5,871,548 | A | 2/1999 | Sanders et al. |
| 5,957,979 | A | 9/1999 | Beckman et al. |
| 5,997,581 | A | 12/1999 | Khalili |
| 6,039,764 | A | 3/2000 | Pottenger et al. |
| 6,074,423 | A | 6/2000 | Lawson |
| 6,074,424 | A | 6/2000 | Perrone et al. |
| 6,080,195 | A | 6/2000 | Colleran et al. |
| 6,136,029 | A | 10/2000 | Johnson et al. |
| 6,162,254 | A | 12/2000 | Timoteo |
| 6,312,473 | B1 | 11/2001 | Oshida |
| 6,423,096 | B1 | 7/2002 | Musset et al. |
| 6,613,092 | B1 | 9/2003 | Kana et al. |
| 6,843,806 | B2 | 1/2005 | Hayes et al. |
| 6,946,001 | B2 | 9/2005 | Sanford et al. |
| 6,981,991 | B2 | 1/2006 | Ferree |
| 7,105,026 | B2 | 9/2006 | Johnson et al. |
| 7,179,295 | B2 | 2/2007 | Kovacevic |
| 2003/0065397 | A1 | 4/2003 | Hanssen et al. |
| 2003/0153981 | A1 | 8/2003 | Wang et al. |
| 2003/0183025 | A1 | 10/2003 | Krstic |
| 2004/0049284 | A1 | 3/2004 | German et al. |
| 2004/0117024 | A1 | 6/2004 | Gerbec et al. |
| 2004/0162619 | A1 | 8/2004 | Blaylock et al. |
| 2004/0172137 | A1 | 9/2004 | Blaylock et al. |
| 2004/0236424 | A1 | 11/2004 | Berez et al. |
| 2005/0042288 | A1 | 2/2005 | Koblish et al. |
| 2005/0246021 | A1 | 11/2005 | Ringeisen et al. |
| 2005/0249625 | A1 | 11/2005 | Bram et al. |
| 2005/0278034 | A1 | 12/2005 | Johnson et al. |
| 2007/0088443 | A1 | 4/2007 | Hanssen et al. |
| 2008/0021566 | A1* | 1/2008 | Peters et al. ............ 623/20.16 |

FOREIGN PATENT DOCUMENTS

| | | |
|---|---|---|
| EP | 1570812 A1 | 9/2005 |
| FR | 2772593 A1 | 6/1999 |
| WO | WO 8302555 A1 | 8/1983 |
| WO | WO 0205732 A1 | 1/2002 |
| WO | WO 03101647 A2 | 12/2003 |
| WO | WO 2005107829 A2 | 11/2005 |
| WO | WO 2006014294 A1 | 2/2006 |
| WO | WO 2007097949 A2 | 8/2007 |

OTHER PUBLICATIONS

A. Laptev et al., Study of Production Route for Titanium Parts Combining Very High Porosity and Complex Shape, Power Metallurgy, 2004, 8 pages, vol. 47 No. 1.

* cited by examiner

POROUS TITANIUM TIBIAL SLEEVES AND THEIR USE IN REVISION KNEE SURGERY

RELATED APPLICATIONS

This application claims priority to U.S. patent application No. 61/058,256, filed Jun. 3, 2008, the disclosure of which is incorporated herein in its entirety.

TECHNICAL FIELD

The invention concerns, inter alia., porous titanium tibial sleeves and their use in revision knee surgery.

BACKGROUND

Knee replacement surgery typically requires the replacement of the distal end of the femur and the proximal end of the tibia. Implant loosening, infection, and device wear are well-documented failure modes of primary knee arthroplasty. In cases where the primary implants fail, a secondary operation (i.e., revision surgery) is required to replace the faulty device. The factors associated with device failure, including infection and osteolysis, often lead to a deterioration of bone quality in proximity to the implanted knee replacement devices. Upon removal of the faulty device, large bone defects are often encountered on both the tibia and the femur. These defects are often characterized by large cavitary voids along with cortical rim defects. Traditionally, treatment of these defects required the removal of a large amount of stable cortical bone to facilitate the implantation of a metal replacement for the bone defect.

Revision knee arthroplasty has existed since the first primary knees failed; bone loss associated with revision surgery is therefore not a new problem. Noiles et. al., U.S. Pat. No. 4,846,839 ("the 839 patent"), discloses a method for affixing a prosthesis to bone that incorporates oval-shaped terraces conforming generically to the anatomy of the proximal tibia. The geometry of the device transfers stresses to the bone in a manner that generally corresponds to the types of stress transfers that occur in natural bone. The 839 patent also states that a coating or roughened surfaces can be applied to the stepped tibial sleeves to improve fixation with the bone.

Blaylock et al., U.S. Published Patent Application No. 200410162619 ("the 619 application"), describe a tibial augment system to replace bone defects that incorporates cone-shaped augments made of a highly porous tantalum material. The intent of the device is said to be minimizing bone loss while providing a stable basis for a tibia tray implant. The device of the 619 application, however, does not appear to incorporate a stepped design, therefore calling into question its ability to transfer stresses from the implant to the bone. In addition, the device of the 619 application does not appear to contain a means for mechanically fixing the tibial tray to the tibial cone augment. Rather, the tibial tray is cemented to the tibial augment that provides for a decreased rotational stability than a mechanical lock.

Although much research has been invested into devices that can be used when a primary knee implant fails, there are still important improvements that are needed. Areas of needed improvements include improved transfer of stresses to the bone in a manner that generally corresponds to the types of stress transfers that occur in natural bone and improved rotational stability.

SUMMARY

One aspect of the invention concerns monolithic foam sleeves that comprise titanium or titanium alloy foam having a porosity of 50 to 85% and possess a proximal surface,
a distal end,
an interior wall that defines an interior channel and extends from the proximal surface to the distal end; and
a terraced outer surface that tapers such that said sleeve is widest at the proximal surface and most narrow at the distal end.

In some preferred embodiments, the sleeve is constructed of a material that has a porosity of 60 to 80%. In certain sleeves, the titanium alloy is Ti6Al4V. In some embodiments, commercially pure titanium (CP titanium) is used to construct the foam sleeve.

The shape and size of the sleeve can generally correspond to the shape of cancellous bone associated with a proximal end of a tibia of a mammal. In some sleeves, the interior channel has a substantially oval cross-section. In other sleeves, the interior channel has a substantially round cross-section or a substantially triangular cross-section.

Certain sleeves have the additional feature of a tray adapter that is affixed to the interior channel of the sleeve. The tray adapter can have a channel in communication with the interior channel of the sleeve, and an exterior geometry that generally corresponds to the shape of the interior channel of the sleeve. In some embodiments, the channel in the tray adaptor is offset medially or laterally relative to the center of the interior channel of said sleeve.

Another feature that can be present in the sleeves of the instant invention are one or more titanium inserts that have a porosity of less than 10% and are positioned within the sleeve such that a portion of said insert is exposed within said outer surface. Such inserts can provide an area of increased strength that is useful, for example, in accommodating a screw or other attachment hardware.

Other aspects of the invention concern methods of forming a tibial implant comprising sintering a tibial tray to a monolithic foam tibial sleeve, wherein said tibial sleeve comprises titanium or titanium alloy foam having a porosity of 50 to 85% and possesses:

a proximal surface,
a distal end,
an interior wall that defines an interior channel and extends from the proximal surface to the distal end; and
a terraced outer surface that tapers such that said sleeve is widest at the proximal surface and most narrow at the distal end.

Yet other aspects of the invention concern methods of replacing a knee prosthesis device comprising affixing a tibia component of said device to the tibia, said device having a monolithic foam sleeve, said sleeve comprising titanium or titanium alloy foam having a porosity of 50 to 85% and possessing a proximal surface,
a distal end,
an interior wall that defines an interior channel and extends from the proximal surface to the distal end; and
a terraced outer surface that tapers such that said sleeve is widest at the proximal surface and most narrow at the distal end.

BRIEF DESCRIPTION OF THE DRAWINGS

FIG. 7 presents (A) and (B) embodiments that are variations of the embodiment shown in FIG. 1A; (C) an embodiment that is a variation of FIG. 1B; and (D) a taper adaptor embodiment that is smaller in thickness compared to the embodiments in FIGS. 4 and 5.

DETAILED DESCRIPTION OF ILLUSTRATIVE EMBODIMENTS

In revision knee surgery, establishing a stable tibial base is often critical to long-term implant survivorship. The present invention provides tibial implant devices that can be used to fill cavitary tibia defects and establish a stable tibial plateau while minimizing the loss of healthy bone. Preferred devices are made of a highly porous titanium structure that facilitates bone ingrowth. The devices preferably provide a stable basis for replacement tibial components to be fixed to definitively through mechanical interlock or cementation.

The present invention includes a family of improved tibial sleeves, based upon the design of the MBT Revision sleeves (M.B.T™(Mobile Bearing Tibial) sleeves are marketed by DePuy Orthopaedics Inc.). The basic geometry of the sleeves is described by Noiles et al. in U.S. Pat. No. 4,846,839, and is incorporated by reference herein in its entirety. Unlike prior devices, the sleeves of the present invention are made of a highly porous titanium material that has a high coefficient of friction on the exterior bone-contacting surface to encourage bone ingrowth. By using a material that is highly porous throughout, bone growth preferably is encouraged in a manner substantially greater to any coating or roughened surface finish mentioned in the prior art.

The internal surface of the instant sleeves, in contrast to the outer surfaces, is generally relatively smooth and provides a substrate for cementation of a tibial tray or permanent fixation of a tray adapter. In some embodiments, the interior wall has a low coefficient of friction of 0.3-0.7). In contrast, in some embodiments, the outer surfaces of the device can have a coefficient of friction of 0.7-1.5).

A tray adapter can be permanently fixed to the porous titanium sleeve through a sintering process. The adapter preferably has an exterior geometry that is designed to match the interior geometry of the sleeve and an interior geometry designed to mate with the revision tray taper. Sintering processes are well known to those skilled in the art.

Figure 1A:
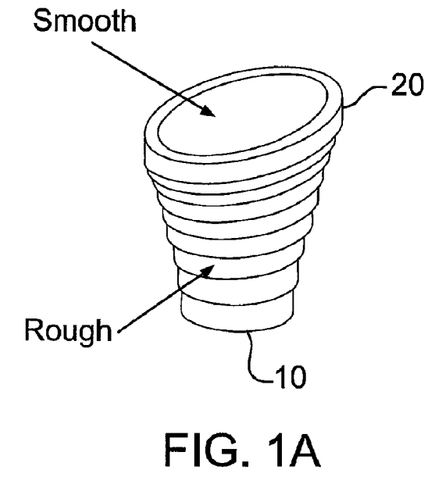
FIG. 1A presents an example of a tibial sleeve.
Figure 1B:
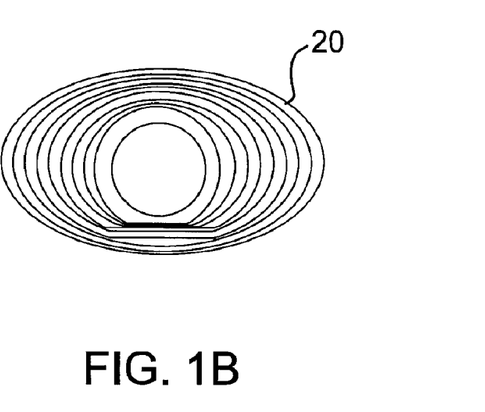
FIG. 1B shows the sleeve of FIG. 1A having substantially oval layers.
Figure 2A:
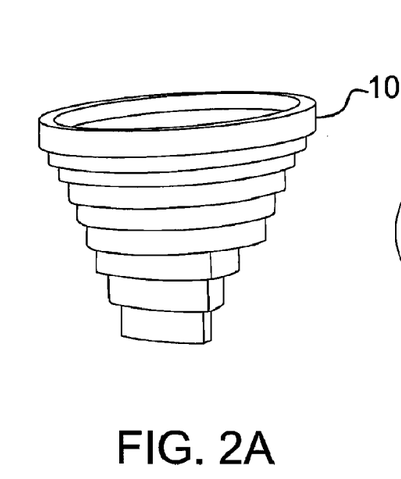
FIG. 2A presents an example of a tibial sleeve.
Figure 2B:
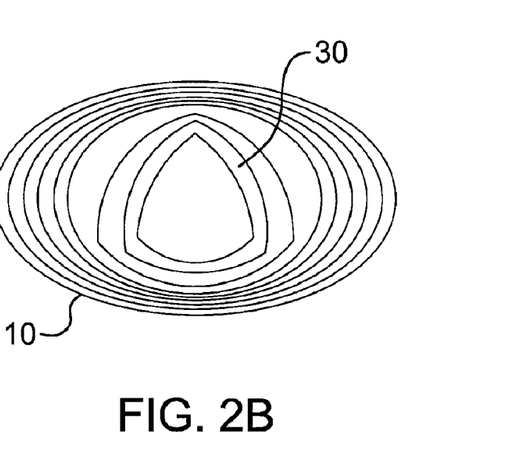
FIG. 2B shows the sleeve of FIG. 2A having a distal geometry becoming substantially triangular to better match the internal geometry of the tibial canal.

The devices of the instant invention can be formed from a plurality of layers, with the geometry of each layer optimized (for example, oval shaped) to replicate the internal geometry of a tibia. Examples of tibial sleeves, 10, are shown in FIGS. 1A, 2A, 3A, and 6. The sleeve shown in FIG. 1B has a plurality of layers, 20, whose distal geometry becoming substantially circular to match the internal geometry of the tibial canal. The geometry of this sleeve is essentially identical to that defined by the MBT revision tibial sleeves. The embodiment shown in FIG. 2B has a plurality of layers, 30, whose distal geometry becomes substantially triangular to better match the internal geometry of the tibial canal.

Figure 3A:
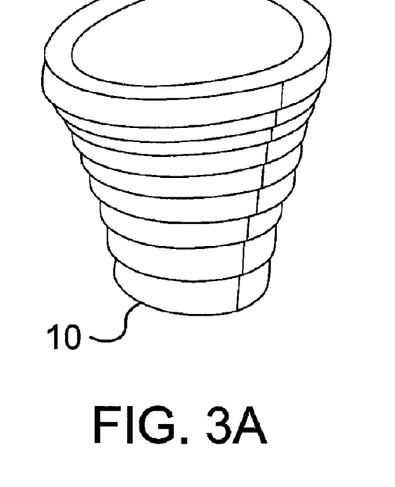
FIG. 3A presents an example of an example of a tibial sleeve.
Figure 3B:
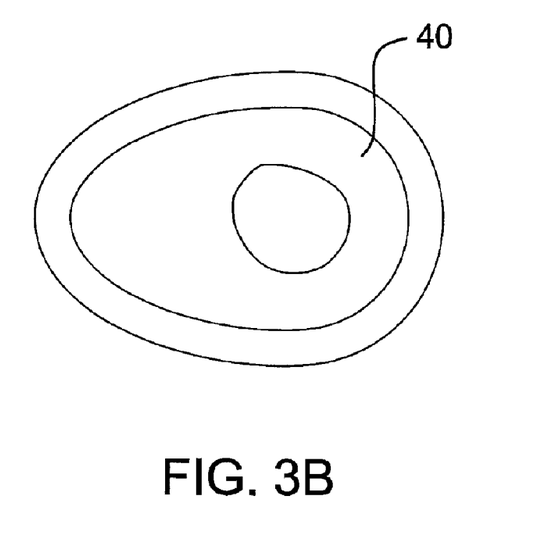
FIG. 3B shows a half sleeve for use with a defective tibial component where the cavitary or peripheral rim defects are only present on either the medial or lateral side of the tibia.

Occasionally, following removal of a defective tibial component, cavitary or peripheral rim defects are only present on either the medial or lateral side of the tibia. To avoid excessive bone loss, the tibia sleeve can be offset medially or laterally. FIG. 3B shows the tibial sleeve, 40, offset to be a void filler for either the medial or lateral side only. The device is essentially a "half sleeve" with the sleeve being eccentric in only a single side of the device.

Figure 4:
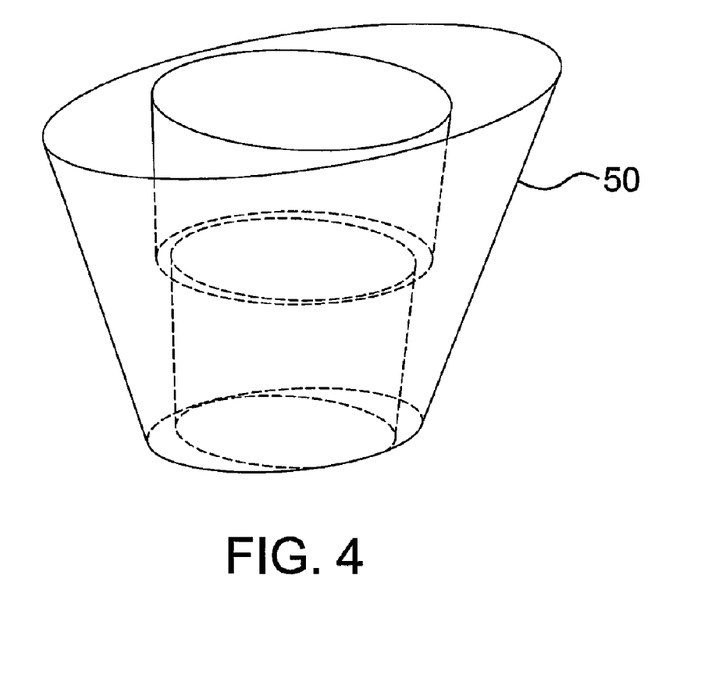
FIG. 4 shows an example of a standard tray adapter.
Figure 5:
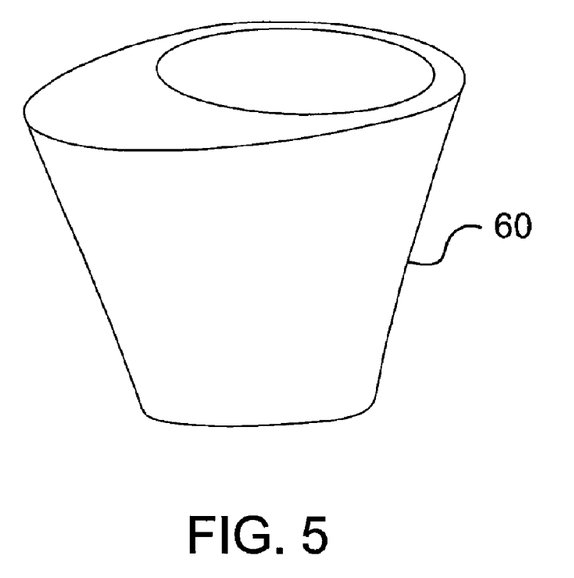
FIG. 5 shows an example of a half sleeve tray adapter.

The structures described above incorporate a rough finish on the exterior bone-contacting surface and a smooth finish internally. A tibial tray can be attached to the sleeve by cementation. If definitive mechanical fixation is required between the tibial sleeve and the tibial tray, a tray adapter can be used. The tray adapter facilitates a tapered attachment between the sleeve and the tibial tray. An exemplary adapter, 50, is shown below in FIG. 4 and an exemplary half sleeve adapter, 60, is shown in FIG. 5.

Figure 6:
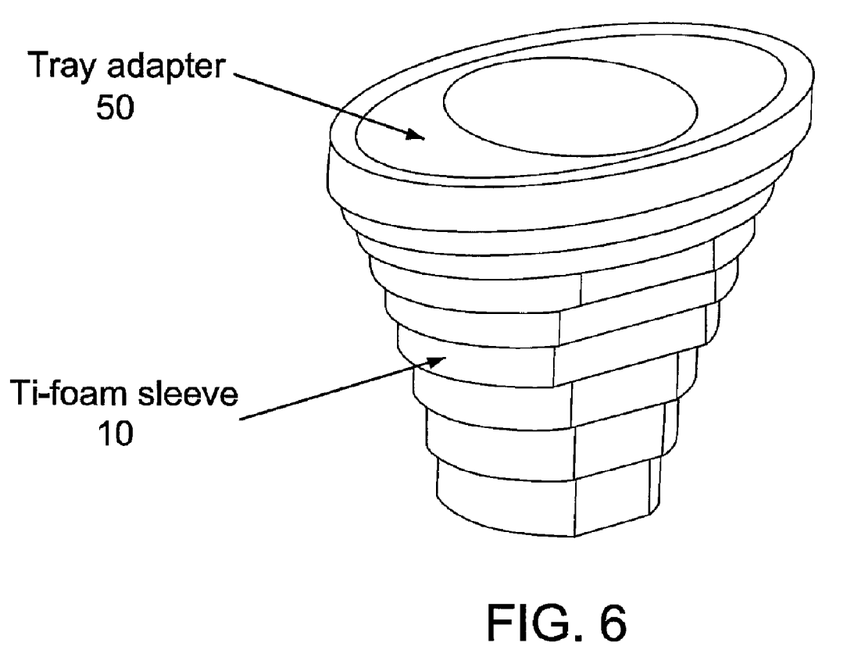
FIG. 6 presents an example of a sleeve with taper adapter.
Figure 7A:
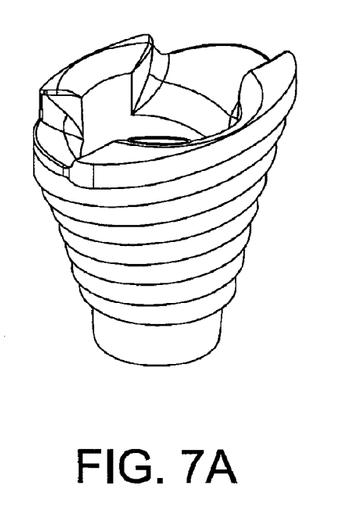
Figure 7B:
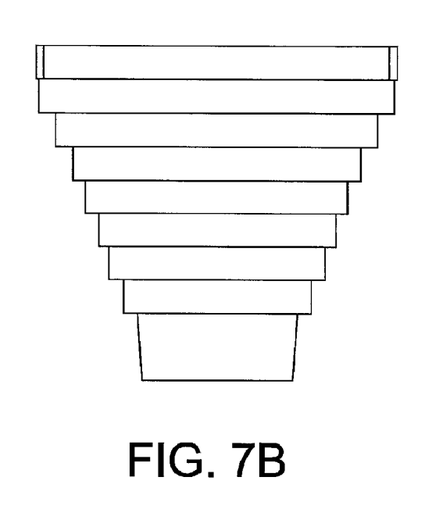
Figure 7C:
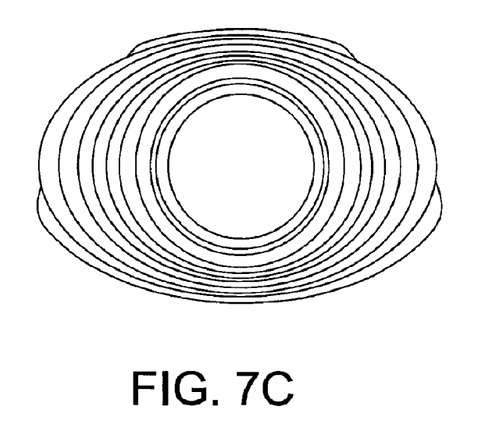
Figure 7D:
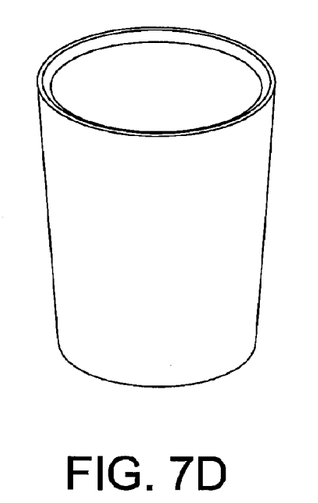

The tray adapter generally has an exterior geometry that matches the interior geometry of the porous sleeve. The adapter can be press-fit into the sleeve and after the sintering process the two bodies become mechanically fixed. The interior geometry of the sleeve adapter can be identical to that of the MBT sleeves and facilitates mechanical fixation to the tibial tray by taper junction. The adapter can be formed from titanium or titanium alloy to improve compatibility with the porous titanium sleeve. A representative sleeve adapter assembly, 50, is shown in FIG. 6.

The sleeves of the instant invention preferably use highly porous Ti or Ti alloy constructs that have a rough outer surface. The rough surface has an open cell structure for making cancellous bone implants and cell and tissue receptors. This structure has been found to be superior to other porous metallic implant materials whose "porosity" is artificially produced via some form of surface treatment that does not result in a truly complete, open porosity. However, without any further treatment such implant surfaces typically are not sufficiently rough and such a surface roughness is an important structural property for initial stability of cementless fixation devices.

The outer surface of the sleeve can be roughened by conventional salt or sand blasting. Such methods are commonly used to induce a macro surface roughness. In such blasting, the surface may be exposed to a high velocity stream of salt or sand that physically gouges away parts of the surface. Depending on the conditions used, at least the outer 10 or 20 microns are impacted by the process. In the case of salt blasting, residual salt can be removed by an aqueous rinse. Conventional machining or glass bead blasting are typically not preferred due to its high porous nature with the open cell structure of the implants. For example, glass fragments can become intraped and present issues after implant. In addition, traditional machining can reduce the porosity of the surface.

In some embodiments, the inner channel is not subjected to salt or sand blasting and is not as rough as the outer surface. The inner surface can be modified by inserting a metal insert with a relatively smooth surface into the interior channel. Because porosity is more important to the outer surface (for bone ingrowth) than the inner channel, any loss of porosity by this process generally is not as important as a loss at the outer surface.

The Ti or Ti alloy foams can be made, for example, by conventional techniques that mix Ti or Ti alloy powder with a pore-foaming agent (PFA). The powder mixture can be compacted under high pressure to form green bodies. The PFA can be removed from the green body which can then be sintered to form to article.

The Ti or Ti alloy powder also can be present in a wide variety of particle sizes and particle size distributions. Certain preferred particle size ranges are from about 20 µm to about 100 µm, from about 25 µm to about 50 µm, and from about 50 µm to about 80 µm.

The term "CP titanium" refers to commercially pure titanium which is well known to those skilled in the art. CP titanium is an unalloyed titanium. Typically, CP titanium contains over 98% pure titanium.

The term "pore forming agent" refers to a material that can be mixed with a metal powder and removed after the mixture is compacted. Such materials are also known in the art as "pore forming" materials. In some embodiments, the pore forming agents are be removed by a liquid. Suitable liquids include aqueous solutions and water. Pore forming agents include water soluble salts such as sodium chloride, potassium chloride, lithium chloride, potassium sorbate, sucrose, or mixtures thereof. After the extractible particulates are removed, the extraction agent or solvent can be removed via evaporation optionally using heat and/or vacuum.

The pore forming agent (PFA) can be present in a wide variety of particle sizes and particle size distributions suitable to produce a desired pore size and pore size distribution. Certain preferred particle size ranges are from about 200 µm to about 600 µm, from about 200 µm to about 350 µm, and from about 350 µm to about 550 µm. Those skilled in the art will recognize that the proportions of metal powder and PFA will vary depending upon the type of structure sought to be produced. In certain embodiments of the present invention, the ratio of metal powder to PFA is about 40:60 to about 10:90.

After treatment to remove the PFA, the green body typically consists of a metal skeleton, which can be subsequently bonded together through high-temperature sintering process to produce Ti or Ti alloy foams with highly porous structures.

Metal powder and PFA are weighed and their respective densities are used to find the volume of each. These values are used to calculate the volume porosity of the mixture, which is generally given with respect to the PFA. Porosity can be determined by measuring the weight of a sintered sample and calculating its volume using the following formula:

% Porosity=weight/(density of solid metal*volume)
*100.

Porosity can also be determined by analyzing cross-section images. Images are taken of mounted, polished cross-sections of the metal foam material. The metal reflects the light and appears white, while the pores appear black.

The mixtures of metallic powder and pore forming agents can be compacted by uniaxial compacting, multi-axial compacting, or isostatic compacting. The method of compacting each layer of the multilayer article can be selected independently. In some embodiments, the preferred method of compacting is cold isostatic press (CIP).

Sintering techniques are well known to the skilled artisan. In some embodiments, the sintering can be conducted in a temperature range that is about 1000 to 1400° C.

The implant can be cleaned prior to any process step or implantation. The cleaning can be performed, for example, with detergent, deionized (DI) water, and ultrasonic bath in 100% alcohol. Such treatment can be useful in removing grease and dust. Sometimes, it may be desirable to dry the implant in an oven after such cleaning.

Another method of cleaning the article is water jet cleaning (at a pressure of 3000 psi, for example) which can remove any weak connections on the surface pores that might otherwise fall off as debris when the implant surface is subjected to friction such as rubbing.

The cleaned implant can be subjected to heat treatment. In some embodiments, the treatment is at a temperature of at least 800° C. This step typically removes volatile impurities such as titanate residue.

The tibial sleeves of the instant invention can offer combination of advantages not found in the art. These advantages include (1) stress transferring steps of porous titanium to optimize stress transfer and bone ingrowth, (2) a geometry becoming substantially circular or triangular distally to maximize tibia cortical contact while minimizing bone loss, (3) a variation of porous titanium surface roughness optimized for contact with bone, titanium or bone cement, (4) ability to mechanically taper lock highly porous sleeve to tibial tray, and/or (5) highly porous sleeve optimized to fill either a medial or lateral defect without sacrificing good bone.

The invention is illustrated by the following examples that are intended to be illustrative but not limiting.

EXAMPLE 1

A rubber mold is created with a void approximately the shape of the tibial sleeve. A titanium powder/salt powder mixture is placed into the mold. A metal mandrel is placed into the mold and power mixture creating the interior channel of the sleeve. The mold and mandrel assembly is then placed into the isostatic press and compacted into solid form. The solid form is machined to form the final exterior terrace profile. The solid form is immersed in reverse osmosis water to remove the major portion of salt. The taper adapter is press-fit into sleeve. The entire assembly is sintered and entire part shrinks by approximately 13%.

EXAMPLE 2

Example 1 is performed using commercial pure titanium powder (Phelly Materials, Inc. Bergenfield, N.J., USA) particle size: 45-75 µm and NaCl (Fisher Scientific International Inc. Hampton, N.H., USA) particle size: 250-425 µm. The titanium and salt are mixed in a ratio of approximately 25:75 Ti:PFA by volume. The mixture is added to a mold and compressed into a green body at a compaction pressure of 22 ksi. The green body is placed in a water bath until the NaCl dissolved. The resulting metal skeleton is dried at 65° C. for 4 hours, and then sintered at 1204° C. for 2 hrs. A highly porous tibial sleeve results.

EXAMPLE 3

A tray adapter is press fit into the interior channel of the tibial sleeve of Example 2 and the components are sintered together.

What is claimed:
1. A tibial implant comprising:
a monolithic foam sleeve suitable for use in revision knee surgery,
said sleeve composed of that comprises titanium or titanium alloy foam having a porosity of 50 to 85% and possesses
a proximal surface,
a distal end,
an interior wall that defines an interior channel and extends from the proximal surface to the distal end; and
a terraced outer surface that tapers such that said sleeve is widest at the proximal surface and most narrow at the distal end, a titanium insert that has a porosity of less than 10% and is positioned within said sleeve such that a portion of said insert is exposed within said outer surface, and a tray adapter that is affixed to the titanium insert, the tray adaptor having a channel extending therethrough.

2. The tibial implant of claim 1, wherein the shape and size of said sleeve generally correspond to the shape of cancellous bone associated with a proximal end of a tibia of a mammal.

3. The tibial implant of claim 1, wherein the interior channel has a substantially oval cross-section.

4. The tibial implant of claim 1, wherein the interior channel has a substantially round cross-section.

5. The tibial implant of claim 1, wherein the interior channel has a substantially triangular cross-section.

6. The tibial implant of claim 1, wherein said sleeve has a porosity of 60 to 80%.

7. The tibial implant of claim 1, wherein the titanium or titanium alloy is Ti6A14V or CP titanium.

8. The tibial implant of claim 1, wherein said channel in said tray adaptor is offset medially or laterally relative to the center of said interior channel of said sleeve.

* * * * *

UNITED STATES PATENT AND TRADEMARK OFFICE
CERTIFICATE OF CORRECTION

| | |
|---|---|
| PATENT NO. | : 8,382,849 B2 |
| APPLICATION NO. | : 12/476431 |
| DATED | : February 26, 2013 |
| INVENTOR(S) | : Kyle Thomas |

It is certified that error appears in the above-identified patent and that said Letters Patent is hereby corrected as shown below:

In the Claims:

Col. 6, line 58, cancel the text beginning with "said sleeve" to and ending "titanium" and insert the following text --said sleeve composed of titanium--

Signed and Sealed this
Fourteenth Day of May, 2013

Teresa Stanek Rea
*Acting Director of the United States Patent and Trademark Office*